United States Patent [19]

Bertholdt et al.

[11] Patent Number: 5,064,857
[45] Date of Patent: Nov. 12, 1991

[54] LIQUID BISMUTH CONTAINING MEDICINAL PRODUCT, PROCESS FOR PRODUCING IT AND ITS USE

[75] Inventors: Heinz Bertholdt, Memmelsdorf; Dieter Michalczyk, Drosendorf; Guenter Urban, Hallstadt, all of Fed. Rep. of Germany

[73] Assignee: R. Pfleger Chemische Fabrik GmbH, Hallstadt, Fed. Rep. of Germany

[21] Appl. No.: 416,922

[22] Filed: Oct. 4, 1989

[30] Foreign Application Priority Data

Oct. 8, 1988 [EP] European Pat. Off. ........ 88116730.8

[51] Int. Cl.$^5$ ............................................. A61K 31/29
[52] U.S. Cl. .................................................... 514/503
[58] Field of Search ........................................ 514/503

[56] References Cited

U.S. PATENT DOCUMENTS

| 4,801,608 | 1/1989 | Bos et al. | 514/503 |
| 4,956,386 | 2/1990 | McLoughlin | 514/503 |

FOREIGN PATENT DOCUMENTS 0206626  6/1986  European Pat. Off. .
2501787  7/1975  Fed. Rep. of Germany .

*Primary Examiner*—Stanley Friedman
*Attorney, Agent, or Firm*—Richard S. Roberts

[57] ABSTRACT

The invention relates to a liquid, bismuth containing medicinal product for the oral treatment of gastro-intestinal illnesses such as gastritis, ulcers, etc., caused by campylobacter.

The invention provides a closed system, e.g. a single dose container or a multiple dose container with dosing device containing one or more portions of the bismuth containing medicinal product. In addition, a simple, inexpensive production process is proposed, in which the bismuth citrate is suspended in water, slightly heated and, accompanied by the addition of caustic potash solution/aqueous ammonia solution, is dissolved and set to a pH-value between 6.0 and 7.0 Subsequently an aqueous tripotassium citrate-citric acid solution is added and if necessary sterilized. The solution obtained is placed in a multidose container with dosing device, or is initially diluted with water to form a ready to drink solution, portioned into single dose containers and optionally sterilized.

17 Claims, No Drawings

LIQUID BISMUTH CONTAINING MEDICINAL PRODUCT, PROCESS FOR PRODUCING IT AND ITS USE

BACKGROUND OF THE INVENTION

The invention relates to a liquid, bismuth containing medicinal product, to a process for producing it and its use. More particularly the invention relates to a packaged product containing a liquid, citric acid chelated, bismuth containing composition.

Liquid products containing bismuth salts are known, as described in German patent application DE-OS 19 02 168 or European Patent Application EP-A 217 440. The pharmaceutical bismuth products known in the form of solutions or suspensions are available in open systems, e.g. in bottles and are unstable, so that special additives or weight ratios are required. Thus, colloidal, aqueous solutions of tricalcium bismuth dicitrate are also unstable and form a sediment after several portions have been removed. Stable solutions can only be prepared with an excess ammonia solution, but as a result of the strong ammonia smell, these are not accepted by the patient. However, by spray drying, it is possible to obtain from such stabilized solutions a stable form of the colloidal tricalcium bismuth dicitrate complex, which can be used for producing solid medicaments, such as film or chewing tablets, or by redissolving or preparing liquid medicaments which can only be kept for a limited time, as described in German Patent 25 01 787.

In the case of the tricalcium bismuth dicitrate solutions filled into a medicine bottle, it is known that an ammonia excess must be present, but this can be calculated in such a way that the solution stability is not adversely effected by the ammonia loss which necessarily occurs when some of the solution is removed several times daily. However, this has the consequence of the solution smelling of ammonia and is unpopular with patients.

It has also been found that in the case of aqueous solutions it is necessary to add preservatives, so as to make the medicament sufficiently stable.

Another disadvantage of solutions supplied in medicine bottles is the lack of dosing accuracy, because generally no dosing aid, e.g. in the case of a measuring spoon is provided therewith, so that it is necessary to use tea or dessert spoons, which have widely differing dimensions.

In the case of tablets as well, the dosing accuracy of the single or multiple dose is unsatisfactory, because it varies as a function of the degree of homogeneity of the material compressed and the tablet weight.

Another disadvantage of chewing tablets is their long contact with the oral mucosa and the dark coloring caused to the tongue and dental enamel. In addition, the active substance must first dissolve in the saliva or gastric juice in order to enable it to reach the action point of the gastric mucosa. As the active substance can only dissolve after release from the tablet or from the tablet particles formed during chewing, it is frequently locally available in different concentrations. As the solubility of the active substance is also pH-dependent and the pH-conditions in the stomach are subject to intra-individual and inter-individual fluctuations, the active substance released from solid products and therefore the action thereof is not reproducible. It is also pointed out that it is also recommended, in the case of tablets, to subsequently drink liquid, so as to free the oral region from chewing tablet residues. It is clear that such tablets only have limited acceptance by dental prosthesis wearers.

An object of the present invention is to avoid the aforementioned disadvantages of the prior art and to improve the aforementioned medicinal product so that it is more patient-friendly.

The invention is consequently directed at a product which is not only the medically most appropriate application or administration, but which is simultaneously neutral as regards taste and odor and which has a high dosing accuracy with regard to the single and multiple dose. It is clear that the sought medicinal product must also be simple and inexpensive to manufacture and have a good storage stability.

This problem is solved by the improved medicinal product and production process of this invention.

SUMMARY OF THE INVENTION

The invention provides a product which comprises one or more single dose, sealed containers, having disposed therein a pharmaceutically effective amount of a liquid bismuth containing composition, said composition being present in said container or containers in an amount suitable for a single dose oral treatment of gastro-intestinal disorders, said composition being present in said containers or containers substantially in the absence of excess ammonia.

The invention also provides a process for the production of a liquid bismuth containing composition which comprises a.) suspending bismuth subcitrate in water; and b.) heating the suspended bismuth subcitrate for a sufficient time and at a sufficient temperature to dissolve the suspension and then adding sufficient aqueous potassium hydroxide and ammonia solution to attain a pH of from about 6.0 to about 7.0; and c.) adding an aqueous tripotassium citrate-citric acid solution.

DETAILED DESCRIPTION OF THE PREFERRED EMBODIMENT

Surprisingly a closed system in the form of a single dose container (e.g. drinking ampule) or a multidose container (e.g. two-chamber pressure pack with dosing device) for the bismuth-containing medicinal product obviates the problems of the prior art. Therefore, in this case a closed system is superior to an open system in the form of resealable medicine bottles. It has surprisingly been found that a colloidal solution of tricalcium bismuth dicitrate complex requires no ammonia excess, if the odorless system set with ammonia to approximately pH 6 to 7, is introduced into a closed system, e.g. into a single-dose container (e.g. drinking ampule) or into a multidose container (e.g. two-chamber pressure pack with dosing valve). Such devices are known to skilled artisan. It is also possible to sterilize this solution and there is no need to add preservatives, which is unavoidable in the case of a solution in an open multidose container.

An important feature of this invention is that one forms a stable liquid bismuth containing composition in the absence of excess ammonia which has been required by the prior art in order to provide a stable solution. A more preferred composition may be defined as a liquid, citric acid chelated, bismuth containing composition. This may be formed by preparing an aqueous admixture of bismuth ammonium citrate and tripotassium citrate. The preferred maximum ammonia amount is defined by the mol ratio NH$_3$:Bi:citrate=1:0.87:1.17. In the most preferred embodiment, the composition comprises a bismuth (III) - citrate hydroxide complex, ammonium-potassium salt. Such a composition is not a single compound but rather a mixture of citric acid bound bismuth complexes corresponding to the general formula Bi$_x$(OH)$_y$(C$_6$H$_5$O$_7$)$_z$. This is also known as bismuth subcitrate. In the most preferred embodiment the composition of this invention comprises bismuth ammonium citrate in an amount of from about 80 mmol to about 120 mmol; tripotassium citrate in an amount of from about 30 mmol to about 40 mmol and water in an amount of from about 1.0 ml to about 20.0 ml. The foregoing amount of bismuth ammonium citrate is bio-equivalent to about 100 mg to about 140 mg of Bi$_2$O$_3$. Such bio-equivalence is a convenient measure of effectiveness because the actual chelate is not precisely known. The composition may optionally include minor amounts of additives such as flavors, coloring agents and stabilizers. An example of a flavoring agent is menthol and such may be present in an amount of about 0.005 to 0.1 mmol. Exemplary colorants are Sunset Yellow FCF; and EEC Nr. E110 in an amount of about 0.01 to about 0.1 mg. Suitable stabilizers include Parabene in an amount of 0.01 to 0.3 mmol. In the absence of the above optional ingredients, the composition is substantially odorless, tasteless and does not contain excess ammonia.

It is clear that the invention permits a problem-free administration, because the content of a drinking ampule can be ingested in the correct dose and without problems as a result of drinkability. The single dose (e.g. 1 to 2 ml) to be taken from a multidose container with a dosage device can be diluted in random manner with water and can therefore also be ingested without any problem. Obviously the inventive medicinal product can be additionally diluted at random with water or other liquids. Moreover, the liquid form of the inventive medicinal product constitutes the medically most appropriate administration form, because the active substance is made available in an already dissolved state and following administration is available immediately in an optimum disperse form for the gastric mucosa.

Furthermore the inventive medicinal product, both in a single-dose container and in a multidose container with dosing device, has a high dosing accuracy. Advantageously, in the most preferred embodiment, each individual dose contains an active substance quantity corresponding to 100 mg to 140 mg, preferably 120 mg of Bi$_2$O$_3$. A multidose container contains a multiple thereof. There is no need for any external dosing aids.

The inventive production process for the liquid, bismuth-containing medicinal product is also particularly simple and economic, because there is no need for any complicated spray drying, such as is necessary in producing corresponding tablets.

Another aspect of the invention is the use of a closed container containing a single or precise dose multiple portion of a liquid, bismuth containing medicine for the treatment of gastro-intestinal illnesses caused by camplyobacter. Moreover, through the special nature of the dosing, there is no possibility of contamination by foreign bacteria and a change to the medicinal product (ammonia loss), so that the stability, shelf life and usability of the product are negatively influenced.

The following non-limiting examples serves to illustrate the invention.

EXAMPLE 100 mmol of bismuth citrate are suspended in water and mixed in a closed system with an aqueous solution of 70 mmol of potassium hydroxide and 115 mmol of ammonia. After adding an aqueous solution of 35 mmol of tripotassium citrate and approximately 2 mmol of citric acid topping up with water takes place to a final volume of 390 ml. The clear solution is either sterilized by heating in the closed system in undiluted form and then placed in multidose containers with a dosing device, or diluted with water in a ratio of 1:1 and then brought into single-dose containers. As a function of the material characteristics of the container, the diluted solution is sterilized before or after introduction into the single-dose container.

What is claimed is:

1. A product which comprises one or more single dose, sealed containers, having disposed therein a pharmaceutically effective amount of a liquid bismuth containing composition comprising a substantially stable, clear, odor neutral, taste neutral solution of bismuth (III)-citrate-hydroxide complex ammonium-potassium salt having a pH of from about 6.0 to about 7.0 in the absence of a preservative, said composition being present in each of said container or containers in an amount suitable for a single dose oral treatment of gastro-intestinal disorders, said composition being present in said containers or containers substantially in the absence of excess ammonia.

2. The product of claim 1 wherein the composition is a clear, stable solution which is substantially odor and taste free.

3. The product of claim 1 comprising a plurality of attached containers, each capable of being separated from one another without affecting the structural integrity of the other containers.

4. The product of claim 1 which comprises a liquid, citric acid chelated bismuth containing composition.

5. The product of claim 1 wherein said composition comprises a clear, stable, substantially odor free and taste free solution containing an aqueous admixture of bismuth ammonium citrate and tripotassium citrate.

6. The product of claim 5 wherein the bismuth ammonium citrate is present in an amount of from about 80 mmol to about 120 mmol, the tripotassium citrate is present in an amount of from about 30 mmol to about 40 mmol and water is present in an amount of from about 1.0 to about 20.0 ml.

7. A process for the production of a product, said product comprising a liquid bismuth containing composition, said composition comprising a substantially stable, clear, odor neutral, taste neutral solution of bismuth (III)-citrate-hydroxide complex ammonium-potassium salt having a pH of from about 6.0 to about 7.0 in the absence of a preservative, which process comprises:

a.) suspending bismuth subcitrate in water; and b.) heating the suspended bismuth subcitrate for a sufficient time and at a sufficient temperature to dissolve the suspension and then adding sufficient aqueous potassium hydroxide and ammonia solution to attain a pH of from about 6.0 to about 7.0; and c.) adding an aqueous tripotassium citrate-citric acid solution.

8. The process of claim 7 further comprising the subsequent steps of (i) optionally adding additional components selected from the group consisting of water and pharmaceutically acceptable additives; and in either order:
- (ii) sterilizing the composition; and
- (iii) filling the composition into one or more single dose containers and sealing the container or containers.

9. The process of claim 8 wherein step (a) comprises suspending about 100 mmol of bismuth subcitrate in about 150 ml water; and step (b) comprises heating to from about 50°-75° C.; the aqueous potassium hydroxide is a solution of about 70 mmol potassium hydroxide in about 50 ml water and the ammonia solution comprises about 35 mmol ammonia in about 20 ml water, and a pH of about 6.5 is attained; and step (c) comprises about 35 mmol of tripotassium citrate-citric acid in about 100 ml water.

10. A liquid, bismuth containing medicinal product for oral treatment of gastro-intestinal illnesses, caused by campylobacter, characterized by a closed system container having a single dose or multiple doses of a bismuth-containing composition comprising a substantially stable, clear, odor neutral, taste neutral solution of bismuth (III)-citrate-hydroxide complex ammonium-potassium salt having a pH of from about 6.0 to about 7.0 in the absence of a preservative and excess ammonia.

11. A liquid, bismuth containing medicinal product according to claim 10, characterized in that the closed system is a single-dose container containing a single dose of the bismuth-containing medicinal composition.

12. A liquid, bismuth containing medicinal product according to claim 10, characterized in that the closed system is a multidose container has a dosing device and contains a multiple dose of the bismuth-containing medicinal composition.

13. A liquid, bismuth containing medicinal product according to claim 10, characterized in that the closed system comprises the following constituents in the form of a stable, clear solution which is odor and taste neutral;
- a. bismuth ammonium citrate, and
- b. tripotassium citrate, and
- c. water.

14. A liquid, bismuth containing medicinal product according to claim 10, characterized in that the container is made from glass, plastic, metal or combinations thereof.

15. A liquid, bismuth containing medicinal product according to claim 10, characterized in that the single-dose containers contain an active substance equivalent of 100 to 140 mg of $Bi_2O_3$, in 5 to 15 ml water.

16. A liquid, bismuth containing medicinal product according to claim 10, characterized in that the multidose container contains a multiple of the active substance equivalent of 100 to 140 mg of $Bi_2O_3$, in 1 to 5 ml and preferably in 2 ml. water.

17. A process for the production of the liquid, bismuth containing medicinal product according to claim 10, characterized by the following steps:
- a. suspending bismuth subcitrate in water,
- b. heating and dissolving the suspension, accompanied by the addition of aqueous caustic potash solution and ammonia solution, setting a pH-value of about 6.0 to 7.0, and
- c. adding an aqueous tripotassium citrate-citric acid solution,
- d. optionally adding further additives,
- e. optionally adding water,
- f. optionally sterilizing the solution and filling it into a multidose container with dosing device,
- g. optionally filling the solution into a single-dose container, sealing and sterilization thereof.

* * * * *